United States Patent
Sherman et al.

[11] Patent Number: 6,001,100
[45] Date of Patent: Dec. 14, 1999

[54] BONE BLOCK FIXATION IMPLANT

[75] Inventors: Mark Sherman, Staten Island, N.Y.;
Auvo Kaikkonen, Tampere, Finland;
Timo Pohjonen, Tampere, Finland;
Pertti Törmälä, Tampere, Finland

[73] Assignee: Bionx Implants OY, Tampere, Finland

[21] Appl. No.: 08/914,137

[22] Filed: Aug. 19, 1997

[51] Int. Cl.⁶ .................................................. A61B 17/56
[52] U.S. Cl. ............................... 606/72; 606/73; 606/74; 606/75; 606/77; 623/13
[58] Field of Search ................................. 606/72, 75, 73, 606/77, 76, 88, 86, 61; 623/13

[56] References Cited

U.S. PATENT DOCUMENTS

| | | |
|---|---|---|
| 4,744,793 | 5/1988 | Parr et al. . |
| 4,968,317 | 11/1990 | Törmälä et al. . |
| 4,997,433 | 3/1991 | Goble et al. . |
| 5,080,663 | 1/1992 | Mills et al. . |
| 5,108,431 | 4/1992 | Mansat et al. . |
| 5,234,430 | 8/1993 | Huebner ...................................... 606/60 |
| 5,282,802 | 2/1994 | Mahony, III .............................. 606/72 |
| 5,356,435 | 10/1994 | Thein . |
| 5,360,448 | 11/1994 | Thramann . |
| 5,383,878 | 1/1995 | Roger et al. .............................. 606/73 |
| 5,405,359 | 4/1995 | Pierce ........................................ 606/232 |
| 5,425,767 | 6/1995 | Steininger et al. . |
| 5,454,811 | 10/1995 | Huebner ..................................... 606/60 |
| 5,470,334 | 11/1995 | Ross et al. ................................ 606/72 |
| 5,632,748 | 5/1997 | Beck, Jr. et al. ......................... 606/89 |
| 5,766,250 | 6/1998 | Chervitz et al. .......................... 623/13 |

FOREIGN PATENT DOCUMENTS

| | | |
|---|---|---|
| 0 146 398 A2 | 6/1985 | European Pat. Off. . |
| 0 464 479 A1 | 1/1992 | European Pat. Off. . |
| 0 611 557 A2 | 8/1994 | European Pat. Off. . |
| 0 464 479 B1 | 3/1995 | European Pat. Off. . |
| 0 651 979 A1 | 5/1995 | European Pat. Off. . |
| 2 307 179 | 5/1997 | United Kingdom . |
| WO 90 04982 | 5/1990 | WIPO . |
| WO 92 03980 | 3/1992 | WIPO . |
| WO 96 41596 | 12/1996 | WIPO . |

OTHER PUBLICATIONS

Bach, B.R., Potential Pitfalls of Kurosaka Screw Interference Fixation for ACL Surgery, American Journal of Knee Surgery, vol. 2 No. 2 (1989) at 76–82.

Barber, A.F., Burton, E.F., McGuire, D.A. and Paulos, L.E., Preliminary Results of an Absorbable Interference Screw, The Journal of Arthoscopic and Related Surgery, vol. 11, No. 5 (1995) at 537–548.

Bach, B.R., Arthroscopy–Assited Patellar Tendon Substitution for Anterior Cruciate Ligament Insufficiency, American Journal of Knee Surgery, vol. 2, No. 1 (1989) at 3–20.

Daniel, D.M., Akeson, W.H., O'Conner, J.J. (eds.): Knee Ligaments Structure, Function, Injury and Repair, New York Raven Press, 1990 at 11–29.

Kurosoka M., Yoshiya S, Andrish JT: A Biomechanical Comparison of Different Surgical Techniques of Graft Fixation in Anterior Cruciate Ligaments Reconstruction, Am J. Sports Med. 15 (1987) at 225–229.

(List continued on next page.)

*Primary Examiner*—Michael Buiz
*Assistant Examiner*—(Jackie)Tan-Uyen T. Ho
*Attorney, Agent, or Firm*—Kenyon & Kenyon

[57] ABSTRACT

In the present invention, a bioabsorbable implant is described, which implant is manufactured of bioabsorbable polymer, copolymer, polymer alloy or fiber reinforced and/or particle filled composite, which implant is pushed into a hole or drill canal made in a bone, for fixing a bone graft into the drillhole, wherein the implant comprises: (1) at least one elongated body, (2) at least one gripping element to lock the implant into the drillhole, and (3) a platform surface for location of a bone block between the implant and the wall of the drillhole. The implant also may be equipped with (4) an additional arresting means, which effectively prevents the slipping of the bone block out of the drillhole.

15 Claims, 4 Drawing Sheets

OTHER PUBLICATIONS

Rupp, S., Krauss, P.W. and Fritsch, E.W., Fixation Strength of a Biodegradable Interference Screw and a Press–Fit Technique in Anterior Cruciate Ligament Reconstruction with a BPTB Graft, Journal of Arthroscopic and Related Surgery, vol. 13, No. 1 (1977) at 61–65.

Vainionpää, S., Rokkanen, P. and Törmälä, P., Surgical Applications of Biodegradable Polymers in Human Tissues, Progr. Polym. Sci., vol. 14 (1989) at 679–716.

Medical Data International, Inc., Orthopedic and Musculoskeletal Markets: Biotechnology and Tissue Engineering, Feb. 1997 at ES 1–18 and 1–28.

Search Report for PCT/EP98/05223.

BONE BLOCK FIXATION IMPLANT

FIELD OF THE INVENTION

The invention relates to surgical implants manufactured of bioabsorbable (biodegradable) polymer, copolymer, polymer alloy or composite, which implants are used for fixation of a bone block (graft) into a drillhole in a bone, and a method for inserting such implants in a patient.

BACKGROUND OF THE INVENTION

In surgery it is generally known to use a bone-patellar tendon-bone graft, taken from the knee of the patient, to replace the severely damaged anterior cruciate ligament (ACL). In a surgical procedure one bone graft is fixed into a drillhole made from the knee joint into the distal femur and another bone graft is fixed into a drillhole made into the proximal tibia. The bone plugs are fixed into drill holes with bone fixation screws and in most cases with so-called interference screws. A screw is installed into the space between the drillhole and the bone graft to lock the bone graft into the drillhole. The patellar tendon part between the bone blocks acts as a new ACL. The surgical technique of bone-tendon-bone procedure is described, e.g., in Bach, B. R., Potential Pitfalls of Kurosaka Screw Interference Fixation for ACL Surgery, American Journal of Knee Surgery, Vol. 2, No. 2 (1989) at 76–82 (Ref. 1), the disclosure of which is incorporated herein by way of this reference.

The fixation screws, like interference screws, are normally made of metal, like stainless steel or titanium, or of a bioabsorbable polymer, like polylactide. Metallic and/or bioabsorbable polymeric materials and composites, suitable for manufacturing of bone-tendon-bone graft fixation screws, are described in the literature. See, e.g., Barber, A. F., Burton, E. F., McGuire, D. A. and Paulos, L. E., Preliminary Results of an Absorbable Interference Screw, The Journal of Arthroscopic and Related Surgery, Vol. 11, No. 5 (1995) at 537–548 (Ref. 2); and Bach, B. R., Arthroscopy-Assisted Patellar Tendon Substitution for Anterior Cruciate Ligament Insufficiency, American Journal of Knee Surgery, Vol. 2, No. 1 (1989) at 3–20 (Ref. 3), the disclosures of which are incorporated herein by way of this reference.

The use of screws as fixation implants for bone grafts in bone-tendon-bone procedures is complicated by various facts:

- the threads of the screw can cut the bone block to pieces during screw installation if the screw is too big in relation to the bone block and/or if the space between the drillhole and bone block is too small;
- the threads of the screw can damage the tendon during screw installation;
- the bone block (and the tendon) can rotate with the screw during screw installation so that the optimal position of the bone graft is lost and/or the bone graft is damaged;
- divergence of the graft and/or screw can occur; and
- the bioabsorbable screw can break during its insertion.

Such complications like those recited above are discussed in the above three references cited herein.

SUMMARY OF THE INVENTION

Accordingly, it would be advantageous to have a bone-tendon-bone fixation implant that avoids the above complications associated with inserting screws into a drillhole, as with the prior art devices. The present invention surprisingly eliminates to a great extent those problems experienced when using such prior art devices. In the present invention, a bioabsorbable implant is manufactured of bioabsorbable polymer, copolymer, polymer alloy or fiber reinforced or particle filled composite, which implant is pushed into a hole or drill canal made in a bone, for fixing a bone graft into the drillhole, wherein the implant comprises: (1) at least one elongated body, (2) at least one gripping element to lock the implant into the drillhole, and (3) a platform surface for location of a bone block between the implant and the wall of the drillhole. The implant also may be equipped with (4) an additional arresting means to prevent the slipping of the bone block out of the drillhole.

Thus, by using surgical implants made in accordance with the present invention, the above-mentioned difficulties and functional restrictions present in prior art implants for bone-tendon-bone fixation can be eliminated.

BRIEF DESCRIPTION OF THE DRAWINGS

The invention is illustrated in the following specification with reference made to the accompanying drawings. In the drawings.

DETAILED DESCRIPTION OF THE PREFERRED EMBODIMENTS

Figure 1:
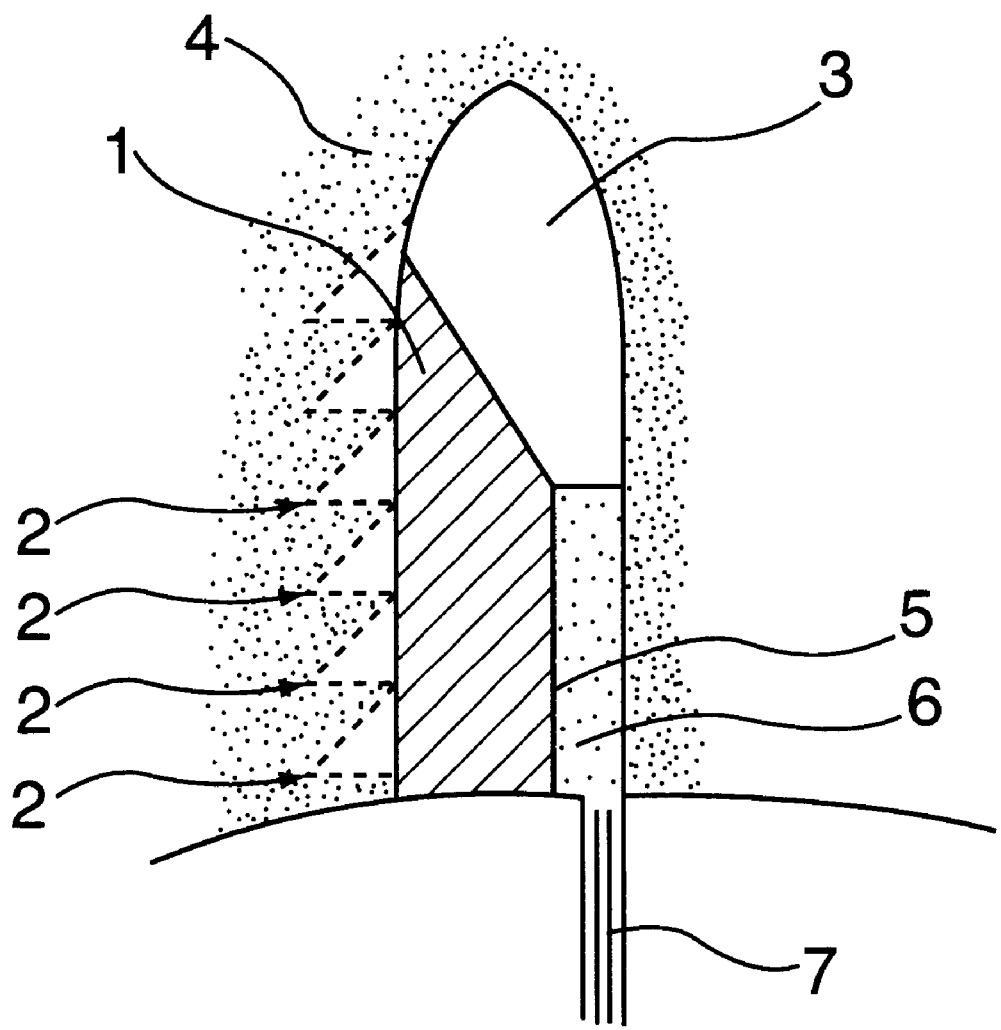
FIG. 1 is a longitudinal cross-sectional figure, showing one embodiment of the implant in accordance with the present invention.

As shown in FIG. 1, a surgical fixation implant in accordance with the invention is comprised of: (a) of an elongated body (1); (b) at least one gripping element (2), which lock(s) the implant into the drillhole (3) in the bone so that the gripping element(s) sink at least partially inside of the bone (4) during the insertion of the implant; and (c) a platform surface (5), on which the bone graft (6) (from which the tendon (7)emerges) is located between the implant (1) and the surface of the drillhole (3). A tight press fit of implant (1) and bone graft (6) into the drillhole (3) is achieved when the maximum thickness of the implant (1) combined with the maximum thickness of the bone graft (6) is greater than the diameter of the drillhole (3).

Figure 2:
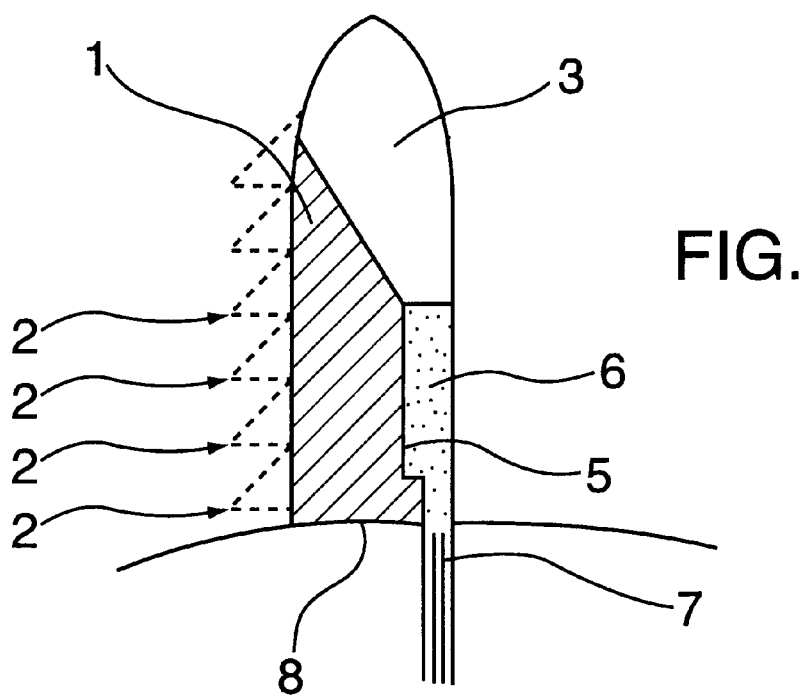
FIG. 2 illustrates is a longitudinal cross-sectional figure, showing a second embodiment of the implant of the invention.

Additionally, according to FIG. 2, the implant (1) can further comprise an arresting means (8) (e.g., a protuberance, barb, threshold, etc.), located in front of or on the proximal part of the platform surface (5). The arresting means effectively prevents the slipping of the bone graft (6) from the drillhole (3) after the bone graft (6) has been pressed into the drillhole with the implant (1) and, at the same time, the arresting means allows the tendon (7) to emerge from the drillhole (3).

Figure 3:
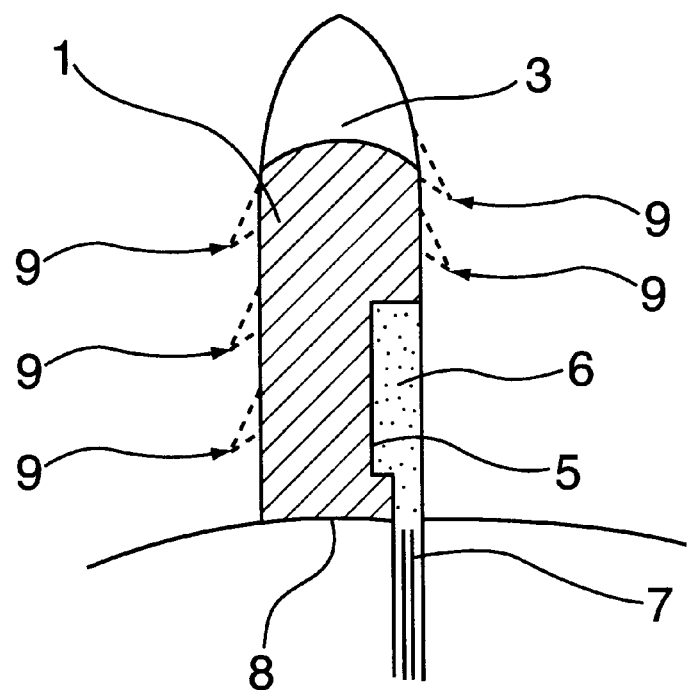
FIG. 3 is a longitudinal cross-sectional figure, illustrating a third embodiment of the implant of the invention.

The gripping elements of the invention, as depicted, e.g., in FIGS. 1 and 2, typically comprise at least one protuberance, thread, transverse ridge, barb, pyramid-like elevation, etc., emerging from the surface of the implant. The geometry of gripping elements is such that the implant (1) slips easily into the drillhole (3) but does not slip back again. According to the advantageous embodiment of the invention shown in FIG. 3, the gripping elements comprise barbs (9) emerging from the surface of the implant (1). The barbs (9) according to FIG. 3 cause only minor resistance when the implant (1) with the bone graft (6) is pushed into the drillhole (3), but the barbs prevent the slippage of the implant (1) back from the drillhole (3) after its insertion. Because the bone graft (6) is locked into the drillhole (3) in relation to the implant (1), post-insertion slippage of the bone graft (6) back from the drillhole (3) is also prevented effectively.

Figure 4:
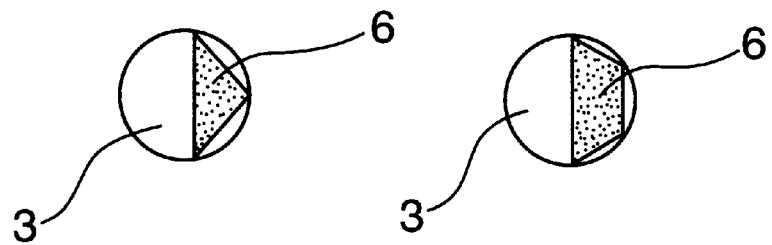
FIG. 4 is a transverse cross-sectional figure, showing typical geometries for bone grafts located in the drillhole of a bone.

FIG. 4 shows typical cross-sections of bone grafts (6) in relation to a drillhole (3) in the bone. As shown by examining the geometries illustrated in FIG. 4, the implant is most advantageously cylindrical in form. The platform surface and the arresting means are then formed to the cylindrical surface of the implant.

Figure 5:
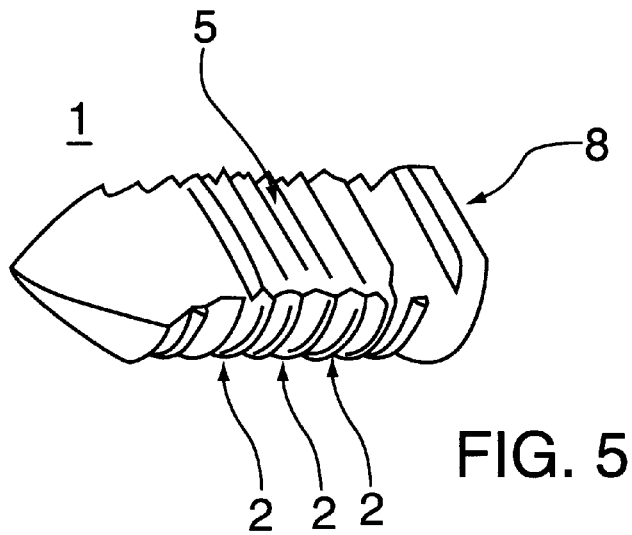
FIG. 5 shows an implant of the present invention, which is equipped with ridge-like gripping elements.

FIG. 5 shows a perspective view of a typical implant (1) of the invention, having circular ridges as gripping elements (2) around the cylindrical body of implant, with a threshold-like arresting means (8) and with a serrated platform surface (5).

Figure 6:
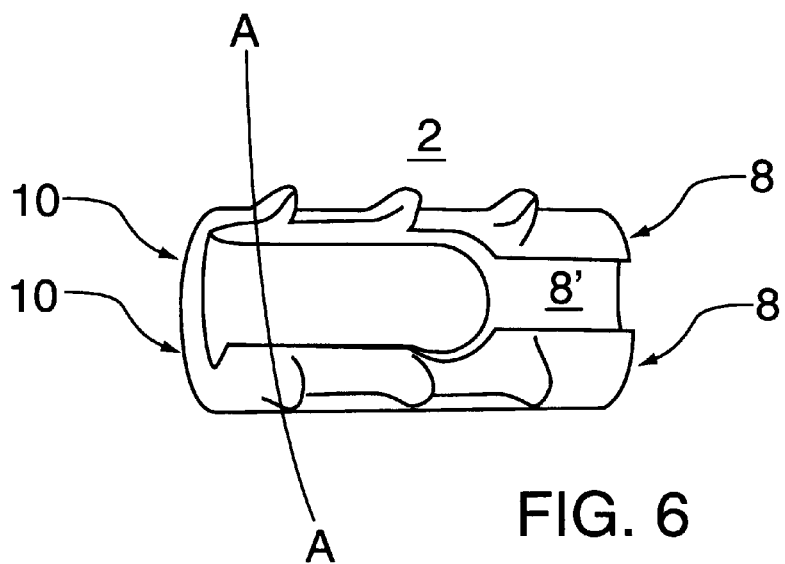
FIG. 6 shows an implant of the present invention, which is equipped with barb-like gripping elements.

FIG. 6 shows a perspective view of another cylindrical implant of the invention, having barbs as gripping elements (2) on the surface of the implant, with an arresting means (8) equipped with a groove (8') for the tendon, and with the platform surface (5) sunk inside of the body of the implant to form the floor of a slot (10) for receiving a bone graft.

Figure 7:
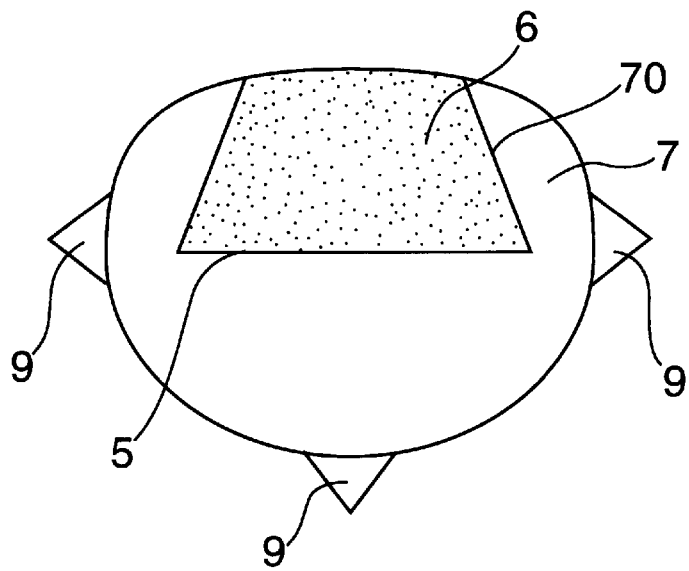
FIG. 7 shows a cross-sectional figure in plane A—A of the implant of FIG. 6 with a bone block.

FIG. 7 is a cross-sectional view of plane A of the implant depicted in FIG. 6, and illustrates the slot (10) inside of the implant (1), the bone graft (6) inside of the slot (10) located on the platform surface (5), and the gripping elements (barbs) (9) on the surface of the implant (1).

Figure 8:
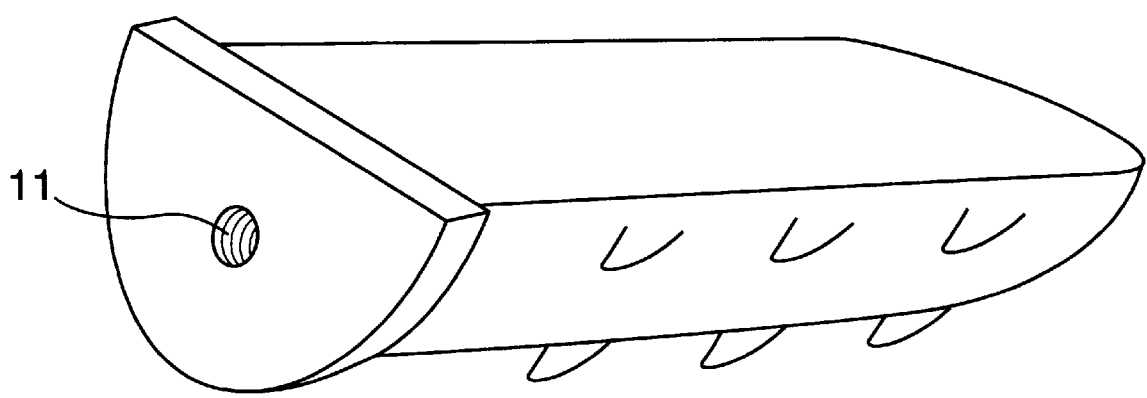
FIG. 8 shows a perspective view of an implant of the present invention with a hole for the tip of an installation instrument.

Under the present invention, the bone block can be attached to the implant prior to their insertion into the drillhole in the bone, or the bone block can be inserted first into the drillhole and then the implant can be inserted into the drillhole. Thus, the implant of the present invention can be pushed arthroscopically into a drillhole in a bone, either along with the bone block or after the bone block is first located inside of the drillhole, using, e.g., one or a combination of the techniques listed immediately below.

the implant is pushed to its place in the drillhole through a tube-like cannula;

a longitudinal hole is made through the implant for receipt of a guide wire, and the implant is pushed into its place in the drillhole along the guide wire; and a small, threaded hole (11) is made in the proximal part of the implant, as is described in the perspective shown in FIG. 8, the tip of a (e.g., bayonet-like) installation instrument is fixed into the hole (11), and the instrument is used to push the attached implant into position in the drillhole.

Likewise, in the case where the bone block is first inserted into the drillhole, the bone block can be pushed arthroscopically into the drillhole in the same manner as described above.

According to an advantageous embodiment of the invention, the implant contains holes or open porosity to facilitate tissue or bone growth inside of the implant. Such holes or pores typically have a diameter from 100 $\mu$m to 2000 $\mu$m. The holes or pores may be filled with cancellous bone of the patient, or with ceramic bone substitute powder or granules (e.g., bioglass), to accelerate their filling with new bone. Such new bone inside of holes or pores of the implant facilitates the final healing of drillhole and the fixation of the bone block inside of the drillhole when the implant biodegrades and disappears from the drillhole.

Thus, by applying implants according to the invention it is possible to efficiently attach and immobilize bone grafts into drill holes in bone, against forces tending to loosen the bone grafts, without having to carry out a time-consuming and risky fixation with a screw, which may damage the bone block and/or the tendon graft fixed to the bone graft.

Fixation implants in accordance with the invention can be manufactured of bioabsorbable (biodegradable or resorbable) polymers, copolymers, polymer alloys or composites, e.g., of poly-$\alpha$-hydroxide acids and other aliphatic biodegradable polyesters, polyanhydrides, polyorthoesters, polyorganophosphatzenes, and other bioabsorbable polymers disclosed in numerous publications, e.g., in Finnish Patent Application Nos. FI-952884 and FI-955547, and PCT Application No. WO-90/04982, the disclosures of which are incorporated herein by reference.

Implants in accordance with the invention can be manufactured of biodegradable polymers by using one polymer or polymer alloy. The implants can also be reinforced by reinforcing the material by fibers manufactured of resorbable polymer or polymer alloy, or biodegradable glassfibers, such as p-tricalciumphosphate fibers, bio-glassfibers or CaAl fibers (cf., e.g., European Patent Application No. EP146398, the disclosure of which is incorporated herein by reference). Ceramic powders can also be used as additives (fillers) in the implants of the present invention, to promote new bone formation.

Implants according to the invention can also contain layered parts comprising, e.g., (a) a flexible surface layer improving the implant's toughness, and/or for releasing drugs or other bioactive substances, and/or operating as a hydrolysis barrier, and (b) a stiff inner layer.

Surgical implants in accordance with the invention can be manufactured of biodegradable polymers and of suitable biodegradable reinforcement fibers by means of various methods used in plastic technology, such as injection molding, extrusion and fibrillation and molding related thereto (cf, e.g., U.S. Pat. No. 4,968,317, the disclosure of which is incorporated herein by reference) or by means of compression molding, wherein the implant pieces are shaped of the raw material by employing heat and/or compression. Also mechanical machining (e.g. cutting, drilling, lathing, grinding etc.) can be used in this regard.

It also is possible to manufacture implants of the invention using the aforementioned polymeric raw materials and dissolving at least part of the polymer in a suitable solvent or softening the polymer by means of that solvent, and then compressing the polymer into an implant piece by means of pressure and/or by means of slight heat, wherein the dissolved or softened polymer is glued to form a macroscopic implant piece wherefrom the solvent is removed by evaporation.

It is natural that the implants of the invention can also contain various additives for facilitating the processability of the material (e.g., stabilizers, antioxidants or plasticizers) or for changing its properties (e.g., plasticizers or ceramic powder materials or biostable fibers, such as carbon fibers) or for facilitating its treatment (e.g., colorants).

According to one advantageous embodiment of the invention, the implant (and/or its surface layer) contains some bioactive agent or agents, such as antibiotics, chemotherapeutic agents, agents activating healing of wounds, growth factor(s), bone morphogenic protein(s), anticoagulant (such as heparin) etc. Such bioactive implants are particularly advantageous in clinical use, because they have, in addition to their mechanical effect, also biochemical, medical and other effects in various tissues.

What is claimed is:

1. A surgical implant for fixing a bone block into a drillhole in a bone, said implant comprising: at least one elongated body manufactured from bioabsorbable polymer, copolymer, polymer alloy or composite; at least one gripping element on the elongated body, for locking the implant into the drillhole; and a platform surface on the elongated body for receiving the bone block, wherein said elongated body, gripping element and platform surface are integrally attached, and said elongated body is capable of being pushed into the drillhole.

2. A surgical implant according to claim 1, further comprising an arresting means for preventing slipping of the bone block out of the drillhole.

3. A surgical implant according to claim 1, wherein said at least one gripping element comprises at least one protuberance.

4. A surgical implant according to claim 1, wherein said at least one gripping element comprises at least one thread.

5. A surgical implant according to claim 1, wherein said at least one gripping element comprises at least one transverse ridge.

6. A surgical implant according to claim 1, wherein said at least one gripping element comprises at least one barb.

7. A surgical implant according to claim 2, wherein said arresting means comprises at least one protuberance.

8. A surgical implant according to claim 2, wherein said arresting means comprises at least one barb.

9. A surgical implant according to claim 2, wherein said arresting means comprises at least one threshold.

10. A surgical implant according to claim 1, wherein said elongated body is cylindrical in form.

11. A surgical implant according to claim 1, wherein said elongated body is porous.

12. A surgical implant according to claim 1, wherein said implant is capable of releasing a drug or other bioactive substance.

13. A method of inserting the surgical implant of claim 1 and a bone block into a drillhole in a bone, comprising the steps of:
   a. attaching the bone block to the elongated body;
   b. pushing the bone block and elongated body into the drillhole; and
   c. locking the implant into the drillhole by means of the gripping means on the implant.

14. A method of inserting the surgical implant of claim 1 and a bone block into a drillhole in a bone, comprising the steps of:
   a. inserting the bone block into the drillhole;
   b. pushing the elongated body into the drillhole;
   c. locking the implant into the drillhole by means of the gripping means on the implant.

15. A method for securing a bone graft in an endosteal tunnel comprising:
   drilling an endoseal bore of a size sufficient to form a space between the bone graft and a wall of the bore when the graft is inserted in the bore;
   positioning the bone graft in the bore such that a space is formed between the graft and a wall of the bore;
   selecting a biocompatible bioabsorbable fixation device comprising at least one elongated body manufactured from bioabsorbable polymer, copolymer, polymer alloy or composite, at least one gripping element on the elongated body, for locking the implant into the bore and a platform surface on the elongated body for receiving the bone block;
   pushing the fixation device into the space between the bone graft and the wall of the bore so that the gripping element contacts the wall of the bore and the platform surface contacts the surface of the bone block and the device is located within the bore so that an interference fit, that resists withdrawal of the graft from the bore, is formed.

* * * * *